United States Patent [19]

Brazdil, Jr. et al.

[11] Patent Number: 5,008,427
[45] Date of Patent: Apr. 16, 1991

[54] AMMOXIDATION OF PARAFFINS

[75] Inventors: James F. Brazdil, Jr., Mayfield Village; Mark A. Toft, Lakewood; Linda C. Glaeser, Lyndhurst, all of Ohio

[73] Assignee: The Standard Oil Company, Cleveland, Ohio

[21] Appl. No.: 289,095

[22] Filed: Dec. 23, 1988

[51] Int. Cl.$^5$ ............................................. C07C 253/24
[52] U.S. Cl. .................................................. 558/319
[58] Field of Search .......................................... 558/319

[56] References Cited

U.S. PATENT DOCUMENTS

| | | | |
|---|---|---|---|
| 3,681,421 | 8/1972 | Barclay et al. | 558/325 |
| 3,686,267 | 8/1972 | Taylor | 558/319 |
| 3,860,534 | 1/1975 | Harris et al. | 558/319 X |
| 4,788,317 | 11/1988 | Gattmann et al. | 558/319 |

FOREIGN PATENT DOCUMENTS 1336136  11/1973  United Kingdom ............... 558/319

Primary Examiner—Joseph Paul Brust
Attorney, Agent, or Firm—C. S. Lynch; D. J. Untener; L. W. Evans

[57] ABSTRACT

Disclosed is a process for making an $\alpha$, $\beta$-unsaturated mononitrile, acrylonitrile or methacrylonitrile, by the catalytic reaction in the vapor phase of a paraffin selected from propane and isobutane with molecular oxygen and ammonia and optionally a gaseous diluent, by catalytic contact of the foregoing reactants in a reaction zone with a catalyst, the feed to said reaction zone containing a mole ratio of said paraffin to $NH_3$ in the rnage from 2.5 to 16 and a mole ratio of said paraffin to $O_2$ in the range from 1 to 10, said catalyst having the elements and the proportions indicated by the empirical formula:

$$VSb_mA_aD_dO_x$$

where
A is one or more Ti, Sn, Fe, Cr, Ga
D is one or more Li, Mg, Ca, Sr, Ba, Co, Ni, Zn, Ge, Nb, Zr, Mo, W, Cu, Te, Ta, Se, Bi, Ce, In, As, B, Mn and
m is 0.8–4
a is 0.01–2
d is 0–2
x is determined by the oxidation state of the cations present, which catalyst has been heated at a calcination temperature of at least 780° C.

12 Claims, No Drawings

AMMOXIDATION OF PARAFFINS

This invention relates to the catalytic ammoxidation of propane and isobutane to α,β-unsaturated mononitriles; i.e., acrylonitrile and methacrylonitrile.

Because of the price differential between propylene and propane an economic incentive exists for the development of a viable catalytic process for conversion of propane to acrylonitrile.

Earlier attempts in the prior art to develop an efficient process for the ammoxidation of propane to acrylonitrile produced either insufficient yields or processes that necessitated adding halogen promoters to the feed. The latter procedure would require not only reactors made of special corrosion resistant materials, but also the quantitative recovery of the promoter. The added costs thus eliminated the advantage of the propane/propylene price differential.

It is an object of the present invention to provide an improved process for the ammoxidation of paraffins to unsaturated mononitriles and the corresponding monoolefins.

It is a further object of the present invention to provide an improved catalytic ammoxidation process for making unsaturated mononitriles from lower paraffins without the necessity of using halogen promoters.

Another object is to provide a process for making a vanadium-antimony oxidic catalyst which during calcination, at temperatures of 780° C. or higher that activate the catalyst composition, minimizes or eliminates the clumping together of particles of the composition to make larger catalyst particles.

Other objects, as well as aspects, features and advantages, of the present invention will become apparent from a study of the accompanying disclosure and the claims.

According to one aspect of the invention there is provided a process for making an α,β-unsaturated mononitrile, acrylonitrile or methacrylonitrile, by the catalytic reaction in the vapor phase of a paraffin selected from propane and isobutane with molecular oxygen and ammonia and optionally a gaseous diluent, by catalytic contact of the foregoing reactants in a reaction zone with a catalyst, the feed to said reaction zone containing a mole ratio of said paraffin to NH₃ in the range from 2.5 to 16 and a mole ratio of said paraffin to O₂ in the range from 1 to 10, said catalyst having the elements and the proportions indicated by the empirical formula:

$$VSb_mA_aD_dO_x$$

where
A is one or more Ti, Sn, Fe, Cr, Ga
D is one or more Li, Mg, Ca, Sr, Ba, Co, Ni, Zn, Ge, Nb, Zr, Mo, W, Cu, Te, Ta, Se, Bi, Ce, In, As, B, Mn and
m is 0.8–4
a is 0.01–2
d is 0–2
x is determined by the oxidation state of the cations present,
which catalyst has been heated at a calcination temperature of at least 780° C.

Calcination temperatures can be as high as 1200° C. Usually, calcination temperatures are in the range from 790°–1050° C. The optimum calcination temperature can vary from composition to composition, but the particular narrow optimum calcination temperature range for a given composition can be determined easily by routine experimentation.

We have discovered that the presence of one of the A elements in the catalyst having the elements and proportions of the foregoing empirical formula minimizes or prevents the clumping of the catalyst particles during the calcination heat treatment in the foregoing temperature range, as compared to a vanadium-antimony oxidic catalyst containing 0.8 to 4 atoms Sb per atom of V but having no A element. This is particularly of practical importance in obtaining a particulate catalyst of a given shape and degree of uniformity. Thus, in catalysts of comparative Examples A, B, G, H, and J, as well as M, the particles of catalyst clumped or sintered together during the calcination at 810° C. or 950° C., while such clumping does not occur in catalysts of the invention during the calcination of the particular catalyst, including each of the specific catalysts of the examples illustrated herein.

Moreover, when employing such catalysts the A element makes it possible to obtain at a given temperature a higher productivity than with a given catalyst of Harris U.S. Pat. No. 3,860,534 which contains only V and Sb oxides. The Harris patent catalysts are water-washed, but the present catalysts can be used with or without water-washing. In any event, an important effect of the present compositions in the ammoxidation process is to make possible a higher productivity of nitrile than when using a corresponding vanadium-antimony oxide catalyst. Thus, at a given reaction temperature, the unwashed catalyst of the present invention is better than the prior art unwashed V-Sb oxide catalyst, and when it is water-washed, it is better than the water-washed V-Sb oxide catalyst of the prior art.

Finally, it has been found that subscript "m" in the empirical formula usually gives best results when it is at least 1.2 and when it is at most 2. We also now prefer that subscript "a" is at least 0.05, and that it is at most 0.5, or even 0.4. Furthermore, especially good results are had when A includes one or more of Sn, Ti and Fe.

What we regard as our invention is the ammoxidation of propane or isobutane to make acrylonitrile or methacrylonitrile using (1) a defined excess of paraffin over both ammonia and molecular oxygen and (2) a catalyst which (a) has the elements and proportions hereinbefore defined and (b) has been heat treated at a calcination temperature at least as high as 780° C.

As used herein "paraffin" designates an acyclic paraffin.

In the present process when applied to propane ammoxidation a small amount of propylene is produced in relation to the unreacted propane in the effluent. Such propane effluent containing propylene in the amount of up to 8 mole percent, but usually no more than 6 mole percent, of the amount of propane plus propylene can comprise the substrate feed to the present process. And in general the C₃ or C₄ alkane feed to the process can contain one or more C₃ to C₄ olefins. The C₃ to C₄ olefin content of the feed to the present ammoxidation process can contain from zero to 8 mole percent of such olefin(s), based on the moles of C₃ to C₄ paraffin plus olefins fed, and this feed can be from any source. Although larger amounts of C₃ to C₄ olefins may be present in the substrate paraffin feed, usual amounts are as stated, and the usual olefin is that corresponding to the particular paraffin fed to the reaction zone of the present process.

In the ammoxidation process of the present invention, the reaction is carried out in the gaseous phase by contacting a mixture of the paraffin, ammonia and molecular oxygen, and inert diluent, if any, conveniently in a fixed bed of the catalyst mixture, or a gravity flowing bed, a fluidized bed or a fast transport reactor mode.

Examples of applicable inert gaseous diluents are $N_2$, He, $CO_2$ and $H_2O$. In the present process in all its embodiments the ratio of inert gaseous diluent to paraffin fed to the reaction zone is usually in the range zero to 5 (more often zero to 3).

The reaction temperature range can vary from 350° to 700° C., but is usually 430° to 520° C. The latter temperature range is especially useful in the case of propane ammoxidation to acrylonitrile.

The average contact time can often be from 0.01 to 10 seconds, but is usually from 0.02 to 10 seconds, more usually from 0.1 to 5 seconds.

The pressure in the reaction zone usually ranges from 2 up to 75, more usually up to 50, psia.

In making the vanadium-antimony oxidic catalyst in a manner such that clumping of the catalyst composition particles is eliminated or substantially reduced during heat treatment and calcination at temperatures of 780° C. and higher we (1) include one or more A elements in a vanadium-antimony oxidic catalyst composition optionally containing one or more D elements in amounts such that the composition contains the elements and the proportions indicated by the empirical formula.

$$VSb_m A_a D_d O_x$$

where
A is one or more Ti, Sn, Fe, Cr, Ga
D is one or more Li, Mg, Ca, Sr, Ba, Co, Ni, Zn, Ge, Nb, Zr, Mo, W, Cu, Te, Ta, Se, Bi, Ce, In, As, B, Mn and
m is 0.8–4
a is 0.01–2
d is 0–2
x is determined by the oxidation state of the cations present, and we (2) calcine said catalyst composition at an upper activation temperature of at least 780° C.

This activation temperature, as before noted can be up to 1200° C. in a given instance, and usual activation temperatures are at least 790° C., while the activation temperature is most often not over 1050° C.

In U.S. Pat. No. 3,860,534 there are disclosed catalysts for the ammoxidation of propane (or other alkanes) using an excess of propane to both ammonia and molecular oxygen wherein the ranges of the paraffin to $NH_3$ and to $O_2$ overlap the ranges of the present process. The catalyst may be mixed with particles of an inert and refractory material, or applied as a layer on the surface of an inert support. Except for such inert materials, the catalyst contains only V, Sb and oxygen. The catalyst is calcined at 350° to 950° C., preferably 700° to 900° C., and particularly 750° to 870° C., and most desirably 790° to 850° C. The essence of the invention is that before use the catalyst is water-washed for long periods in water.

Earlier (earlier filed in the priority country) British patent specification No. 1,336,135, having a common assignee and a common inventor with the aforesaid U.S. patent, discloses inter alia the use of catalysts containing only V and Sb in oxidic form in the ammoxidation of paraffins such as propane at the same alkane to $NH_3$ and $O_2$ ratios, the catalysts being calcined at 300°–950° C., preferably 600° to 850° C. However, the calcined catalysts are not water-washed. The earlier specification also discloses that the catalysts can contain V and Sb and only one other metal. The sole third component disclosed for addition to a V, Sb catalyst is tin, and this is only by way of specific Example III. Calculation of the composition shows that the catalyst has a composition $VSb_{10.3}Sn_{4.5}O_x$. A catalyst of this composition is shown in Comparative Examples G and H herein. Comparative Example J is the catalyst of Comparative Example G which has been water-washed. Results using these catalysts in ammoxidation are shown in Table 3 herein.

U.S. Pat. No. 4,746,641, Guttmann et al. discloses ammoxidation of paraffins including propane and isobutane at ratios of reactants different than the present claims using catalysts that can contain Sn in addition to V and Sb, but these catalysts are calcined at only 700° or 750° C. at the most and are thus not catalysts recited in the present claims regardless of their composition.

British No. 1,336,136, another earlier patent to the common assignee and to a sole inventor who is the common inventor in British No. 1,336,135 and U.S. Pat. No. 3,860,534 is much the same as British No. 1,336,135 but more narrow. Thus, all of the catalysts contain V and Sb in oxidic form with or without only one other metal. The only such other metal identified is tin, which is in Example III, identical to Example III of British No. 1,336,135, already discussed.

Canadian patent No. 901,006 also relates to ammoxidation of propane and isobutane using catalysts of seven different categories. The only pertinent category uses exactly 3 metals in oxidic form in combination, exclusive of the combination V-Sb-Sn. The three are chosen from Sb, Sn, Ti, V and U. No proportions are suggested, except in specific examples. No specific suggestion of, or specific example of, a catalyst having V, Sb and Ti is disclosed.

All of the specific examples of catalysts that follow were made by the method of U.S. Pat. No. 4,784,979, issued Nov. 15, 1988, unless otherwise noted. The compositions were activated to an active catalyst by heating at 810° C. unless another calcination temperature is specifically noted.

The examples are illustrations only and are not to be considered as limiting.

COMPARATIVE EXAMPLE A 27.58 g of $V_2O_5$ powder was slurried in 400 cc of water in a 1 liter beaker. While vigorously stirring, 70 g of a 30% $H_2O_2$ solution in water was slowly added and the $V_2O_5$ began to dissolve. In this step the peroxovanadium ion forms. After about 15 minutes some undissolved $V_2O_5$ remained, and another 70 g of the 30% $H_2O_2$ solution was added with continued stirring. The final dispersion was a red solution with some orange flocculent solids.

72.56 g of powdered $Sb_2O_3$ was added to the foregoing dispersion. The mixture was stirred for about 4 hours with heating in order to reduce the volume by evaporation of water. During this time the slurry formed gradually turned to a deep blue-green, then finally to a blackish green. When the mixture could no longer be stirred it was dried in an oven for about 16 hours at 100° C. Thereafter it was calcined for 8 hours at 650° C., cooled and then crushed and seived to 20–35 mesh. The calcined material was very hard.

A portion of this catalyst was activated by calcining for 1 hour at 810° C. The empirical composition was $VSb_{1.65}O_x$.

COMPARATIVE EXAMPLE B

A portion of the activated catalyst of comparative Example A was washed with water in a Soxhlet extractor for several hours until the wash water appeared colorless. The washed catalyst was then dried by heating at about 100° C. for about 3 hours.

In the other examples that employ water washing the method of Comparative Example B was used, or the catalyst was water-washed with a flowing stream of room temperature water until the wash water appeared colorless.

A series of catalysts of the invention was made according to the general procedure of Comparative Examples A and B, except that the additional elements other than V and Sb were added to the slurry resulting from the reaction of the vanadium compound and the antimony compound before the drying and calcination, unless otherwise noted. Ti was introduced as a $TiO_2$ sol, Co as $Co(NO_3)_2.6H_2O$, Zn as $Zn(NO_3)_2.4H_2O$, Ca as $Ca(NO_3)_2.4H_2O$, Li as $LiNO_3$ in water, Mg as $Mg(NO_3)_2.6H_2O$, Sn as $SnO_2$ sol, Ga as $Ga(NO_3)_3$, Cr as $CrO_3$ in water, Cu as $Cu(NO_3)_2.2.5H_2O$, Fe as $Fe(NO_3)_3.9H_2O$, Mo as $(NH_4)_6Mo_7O_{24}.4H_2O$.

The catalyst example numbers and compositions are as shown in Table A. When a calcining temperature other than 810° C. was used, this temperature is listed. Also noted is whether the catalyst was water-washed or unwashed:

TABLE A

| Example | Empirical Composition | Remarks | Calcination Temp °C. |
|---|---|---|---|
| 1 | $VSb_{1.65}Sn_{0.2}O_x$ | Unwashed | |
| 2 | $VSb_{1.7}Sn_{0.05}O_x$ | Unwashed | |
| 3 | $VSb_{1.7}Sn_{0.05}O_x$ | Washed | |
| 4 | $VSb_{1.65}Sn_{0.1}O_x$ | Washed | |
| 5 | $VSb_{1.7}Sn_2O_x$ | Washed | 950 |
| 6 | $VSbSn_2O_x$ | Washed | 950 |
| 7 | $VSb_{1.7}Sn_{0.2}Cu_{0.05}$ | Washed | |
| 8 | $VSb_{1.7}Sn_{0.05}Ti_{0.05}O_x$ | Washed | |
| 9 | $VSb_{1.7}Sn_{0.1}Cu_{0.05}O_x$ | Unwashed | |
| 10 | $VSb_{1.7}Sn_{0.1}Cu_{0.05}O_x$ | Washed | |
| 11 | $VSb_{1.7}Sn_{0.1}Mo_{0.005}O_x$ | Washed | |
| 12 | $VSb_{1.7}Sn_{0.05}Fe_{0.05}O_x$ | Washed | |
| 13 | $VSb_{1.3}Sn_{0.2}O_x$ | Washed | |
| 14 | $VSb_{1.5}Sn_{0.2}O_x$ | Washed | |
| 15 | $VSb_{1.68}Ti_{0.12}O_x$ | Washed | |
| 16 | $VSb_{1.7}Ti_{0.1}Li_{0.01}O_x$ | Washed | |
| 17 | $VSb_{1.7}Ti_{0.1}O_x$ | Unwashed | |
| 18 | $VSb_{1.7}Ti_{0.1}O_x$ | Unwashed | 750 |
| 19 | $VSb_{1.7}Ti_{0.1}O_x$ | Unwashed | 780 |
| 20 | $VSb_{1.7}Ti_{0.1}O_x$ | Unwashed | 820 |
| 21 | $VSb_{1.7}Ti_{0.1}O_x$ | Washed | |
| 22 | $VSb_{1.7}Ti_{0.1}Mg_{0.05}O_x$ | Washed | |
| 23 | $VSb_{1.7}Ti_{0.1}Ca_{0.01}O_x$ | Unwashed | |
| 24 | $VSb_{1.7}Ti_{0.1}Zn_{0.01}O_x$ | Unwashed | |
| 25 | $VSb_{1.7}Ti_{0.1}Zn_{0.01}O_x$ | Washed | |
| 26 | $VSb_{1.65}Cr_{0.1}O_x$ | Washed | |
| 27 | $VSb_{1.65}Fe_{0.1}O_x$ | Unwashed | |
| 28 | $VSb_{1.65}Fe_{0.1}O_x$ | Washed | |
| 29 | $VSb_{1.7}Sn_{0.05}Fe_{0.05}Ti_{0.05}O_x$ | Unwashed | |
| 30 | $VSb_{1.7}Sn_{0.05}Fe_{0.05}Ti_{0.05}O_x$ | Washed | |
| 31 | $VSb_{1.7}Ga_{0.05}O_x$ | Unwashed | |
| 32 | $VSb_{1.7}Ga_{0.05}O_x$ | Washed | |
| 33 | $VSb_{1.7}Sn_{0.05}Ti_{0.05}Fe_{0.02}Mg_{0.02}Li_{0.02}Zn_{0.01}O_x$ | Washed | |
| K | $VSb_5Sn_{0.1}O_x$ | Unwashed | |
| L | $VSb_5Sn_{0.1}O_x$ | Washed | |
| M | $VSbTi_{6.75}O_x$ | Washed | 950 |

TABLE A-continued

| Example | Empirical Composition | Remarks | Calcination Temp °C. |
|---|---|---|---|
| 34 | $VSbSn_{1.5}O_x$ | Washed | 950 |

COMPARATIVE EXAMPLE G

A composition having the empirical formula of Example 3 of British Patent Specification No. 1336135, $VSb_{10.3}Sn_{4.5}O_x$, was made as follows:

5.15 g of $NH_4VO_3$ were dissolved in 150 cc of hot water with stirring and then 66.13 g of $Sb_2O_3$ was added. The resultant mixture was refluxed overnight. Then 165.95 g of an $SnO_2$ sol containing 21.2 wt. percent $SnO_2$ was added and the resultant mixture was concentrated and then dried overnight in an oven. The dried solid was heated in air at 290° C. for 3 hours, then 425° C. for 3 hours and then 3 hours at 610° C. The composition did not clump at 610° C. A portion was then heated at 810° C. for 1 hour. It clumped to larger, irregular particles.

COMPARATIVE EXAMPLE H

Another portion of the composition of Example G that was heated at 610° C. was then heated at 950° C. for 1 hour. It clumped into larger, irregular particles.

COMPARATIVE EXAMPLE J

This catalyst was a portion of the catalyst of Example G that was water-washed until the wash water appeared colorless.

EXAMPLE 35

This catalyst example was like Example 14 except that calcination was for 1 hour at 810° C. instead of 3 hours. $VSb_{1.5}Sn_{0.2}O_x$. The catalyst was water-washed.

EXAMPLE 36

This catalyst was 92.2 weight % $VSb_{1.5}Sn_{0.2}O_x$ and 7.8 wt. % $SiO_2$ diluent/support. The silica was introduced as tetraethylorthosilicate to the slurry containing the other components. Inclusion of $SiO_2$ in the catalysts of the invention makes them less dense. The catalyst was water-washed.

COMPARATIVE EXAMPLE N

This catalyst was 91.5 wt. % $VSb_{1.5}O_x$ and 8.5 wt. % $SiO_2$ diluent/support. The silica was introduced as in Example 36. The catalyst was water-washed.

The ammoxidation process examples, which are illustrative only, are not to be considered limiting.

In the following ammoxidation examples summarized in Tables 1-3, the catalyst is in a tubular ⅜ inch I.D. stainless steel fixed bed reactor. The reactor is equipped with a preheat leg and is immersed in a temperature controlled molten salt bath. The feed is fed to the catalyst for one hour before collection of product, unless otherwise noted; the runs of each example last 30-60 minutes during which the product is collected for analysis. The fixed mole ratios were 5 propane/1$NH_3$/2$O_2$/1$H_2O$, unless other ratios are noted in the footnotes.

As will be evident to those skilled in the art, various modifications of this invention can be made or followed in the light of the foregoing disclosure and discussion without departing from the spirit and scope of the disclosure or from the scope of the claims.

TABLE 1

| Example | Catalyst Example | Temp. °C. | CT Secs[4] | Percent Propane Conversion | Propane: Mole % Conversion to | | | % Selectivity[1] | | Productivity # AN/# Cat per Hour |
|---|---|---|---|---|---|---|---|---|---|---|
| | | | | | AN[2] | $C_3=$[3] | AN + $C_3=$ | AN | AN + $C_3=$ | |
| C | A | 470 | 1.3 | 12.4 | 5.2 | 2.3 | 7.5 | 41.6 | 60.5 | 0.036 |
| D | B | 470 | 1.3 | 8.3 | 5.3 | 0.4 | 5.7 | 63.5 | 68.9 | 0.036 |
| E | B | 470 | 2.0 | 11.4 | 7.2 | 0.4 | 7.6 | 62.9 | 66.5 | 0.029 |
| 37 | 1 | 470 | 1.3 | 14.5 | 7.1 | 1.8 | 8.9 | 48.7 | 61.3 | 0.048 |
| 38 | 2 | 470 | 1.2 | 13.9 | 7.6 | 1.2 | 8.9 | 54.9 | 63.8 | 0.052 |
| 39 | 3 | 470 | 1.1 | 13.7 | 8.2 | 0.7 | 8.8 | 59.4 | 64.4 | 0.055 |
| 40 | 4 | 470 | 1.0 | 14.1 | 8.3 | 0.8 | 9.2 | 59.1 | 65.1 | 0.068 |
| 41 | 5 | 470 | 1.1 | 13.2 | 6.6 | 0.5 | 7.1 | 50.4 | 54.1 | 0.044 |
| 42 | 6 | 470 | 0.9 | 12.1 | 6.0 | 0.5 | 6.5 | 50.0 | 53.8 | 0.040 |
| 43 | 7 | 470 | 1.4 | 14.3 | 8.8 | 0.5 | 9.3 | 61.3 | 64.9 | 0.060 |
| 44 | 8 | 470 | 1.3 | 14.1 | 8.5 | 0.6 | 9.1 | 60.5 | 64.9 | 0.057 |
| 45 | 9 | 470 | 1.3 | 14.2 | 7.4 | 1.2 | 8.6 | 52.0 | 60.1 | 0.050 |
| 46 | 10 | 470 | 1.3 | 14.3 | 8.8 | 0.6 | 9.3 | 61.3 | 65.2 | 0.059 |
| 47 | 11 | 470 | 1.2 | 14.1 | 8.0 | 0.9 | 8.9 | 56.7 | 62.9 | 0.053 |
| 48 | 12 | 470 | 1.4 | 14.5 | 8.6 | 0.5 | 9.2 | 59.7 | 63.3 | 0.058 |
| 49[5] | 13[6] | 460 | 1.3 | 14.5 | 8.5 | 0.7 | 9.3 | 58.9 | 64.0 | 0.057 |
| 50[5] | 14[6] | 460 | 1.2 | 12.6 | 8.0 | 0.3 | 8.3 | 63.7 | 65.9 | 0.055 |

[1] Selectivity based on propane
[2] AN is Acrylonitrile
[3] $C_3=$ is Propylene
[4] Contact Time, Seconds
[5] 5 Propane/0.88 NH$_3$/20$_2$/1 H$_2$O
[6] Calcined for 3 hours

TABLE 2

| Example | Catalyst Example | Temp. °C. | CT Secs[4] | Percent Propane Conversion | Propane: Mole % Conversion to | | | % Selectivity[1] | | Productivity # AN/# Cat per Hour |
|---|---|---|---|---|---|---|---|---|---|---|
| | | | | | AN[2] | $C_3=$[3] | AN + $C_3=$ | AN | AN + $C_3=$ | |
| 51 | 15 | 470 | 1.2 | 14.0 | 8.3 | 0.6 | 8.9 | 59.2 | 63.7 | 0.056 |
| 52 | 16 | 470 | 1.4 | 14.4 | 8.6 | 0.6 | 9.1 | 59.6 | 63.6 | 0.058 |
| 53 | 17 | 470 | 1.4 | 13.9 | 8.1 | 0.9 | 9.0 | 58.1 | 65.0 | 0.056 |
| F | 18 | 470 | 1.7 | 11.9 | 3.5 | 1.8 | 5.3 | 29.3 | 44.4 | 0.023 |
| 54 | 19 | 470 | 1.7 | 13.8 | 7.0 | 1.0 | 8.1 | 50.8 | 58.4 | 0.048 |
| 55 | 20 | 470 | 1.2 | 13.3 | 7.5 | 1.1 | 8.6 | 56.1 | 64.4 | 0.051 |
| 56 | 21 | 470 | 1.4 | 13.2 | 8.0 | 0.5 | 8.4 | 60.1 | 63.8 | 0.054 |
| 57 | 22 | 470 | 1.4 | 13.9 | 8.2 | 0.6 | 8.8 | 59.1 | 63.0 | 0.055 |
| 58 | 23 | 470 | 1.3 | 14.2 | 7.7 | 1.1 | 8.8 | 54.2 | 62.1 | 0.052 |
| 59 | 24 | 470 | 1.5 | 14.1 | 7.2 | 1.3 | 8.6 | 51.5 | 60.9 | 0.049 |
| 60 | 25 | 470 | 1.4 | 12.0 | 7.1 | 0.5 | 7.6 | 58.6 | 63.0 | 0.048 |
| 61 | 26 | 460 | 1.2 | 13.4 | 6.9 | 0.9 | 7.8 | 51.3 | 58.0 | 0.047 |
| 62 | 27 | 470 | 1.1 | 14.0 | 6.7 | 1.7 | 8.4 | 47.8 | 60.2 | 0.046 |
| 63 | 28 | 460 | 1.0 | 13.3 | 8.1 | 0.5 | 8.6 | 60.7 | 64.3 | 0.055 |
| 64 | 29 | 470 | 1.4 | 14.8 | 8.1 | 1.0 | 9.2 | 54.8 | 61.9 | 0.054 |
| 65 | 30 | 470 | 1.5 | 14.4 | 8.6 | 0.7 | 9.3 | 60.1 | 64.6 | 0.058 |
| 66 | 31 | 470 | 1.2 | 14.4 | 7.0 | 1.6 | 8.6 | 48.3 | 59.7 | 0.047 |
| 67 | 32 | 470 | 1.3 | 13.7 | 7.3 | 1.0 | 8.3 | 52.9 | 60.4 | 0.050 |

[1] Selectivity based on propane
[2] AN is Acrylonitrile
[3] $C_3=$ is Propylene
[4] Contact Time, Seconds

TABLE 3

| Example | Catalyst Example | Temp. °C. | CT Secs[4] | Percent Propane Conversion | Propane: Mole % Conversion to | | | % Selectivity[1] | | Productivity # AN/# Cat per Hour |
|---|---|---|---|---|---|---|---|---|---|---|
| | | | | | AN[2] | $C_3=$[3] | AN + $C_3=$ | AN | AN + $C_3=$ | |
| 68 | 33 | 470 | 1.3 | 14.4 | 8.4 | 0.6 | 9.0 | 57.9 | 62.1 | 0.057 |
| P | G | 470 | 2.6 | 12.5 | 3.8 | 1.6 | 5.4 | 30.5 | 43.0 | 0.012 |
| Q | H | 470 | 2.6 | 13.2 | 3.5 | 2.2 | 5.6 | 26.2 | 42.7 | 0.010 |
| R | J | 470 | 2.6 | 11.1 | 3.6 | 1.3 | 4.9 | 32.8 | 44.7 | 0.011 |
| S | K | 460 | 1.3 | 6.3 | 2.6 | 1.0 | 3.6 | 40.8 | 57.0 | 0.017 |
| T | L | 460 | 1.1 | 5.6 | 3.1 | 0.5 | 3.5 | 54.5 | 62.9 | 0.020 |
| U[5] | M | 460 | 1.7 | 11.7 | 3.8 | 0.7 | 4.4 | 32.2 | 37.9 | 0.026 |
| 69[5] | 34 | 460 | 1.1 | 13.4 | 7.0 | 0.5 | 7.5 | 52.1 | 56.0 | 0.047 |
| 70[5] | 35 | 460 | 1.4 | 14.2 | 8.5 | 0.5 | 9.0 | 59.9 | 63.5 | 0.057 |
| 71[5] | 36 | 460 | 1.2 | 13.7 | 7.7 | 0.5 | 8.2 | 56.2 | 59.7 | 0.053 |

TABLE 3-continued

| Example | Catalyst Example | Temp. °C. | CT Secs[4] | Percent Propane Conversion | Propane: Mole % Conversion to | | | % Selectivity[1] | | Productivity # AN/# Cat per Hour |
|---|---|---|---|---|---|---|---|---|---|---|
| | | | | | AN[2] | $C_3=$[3] | AN + $C_3=$ | AN | AN + $C_3=$ | |
| V[5] | N | 460 | 1.3 | 9.2 | 5.3 | 0.5 | 5.8 | 56.9 | 62.6 | 0.036 |

[1] Selectivity based on propane
[2] AN is Acrylonitrile
[3] $C_3=$ is Propylene
[4] Contact Time, Seconds
[5] 5 Propane/0.88 NH$_3$/2O$_2$/1 H$_2$O

We claim:

1. A process for making an α,β-unsaturated mononitrile, selected from acrylonitrile and methacrylonitrile, by the catalytic reaction in the vapor phase of a paraffin selected from propane and isobutane with molecular oxygen and ammonia and optionally a gaseous diluent, by catalytic contact of the foregoing reactants in a reaction zone with a catalyst, the feed to said reaction zone containing a mole ratio of said paraffin to NH$_3$ in the range from 2.5 to 16 and a mole ratio of said paraffin to O$_2$ in the range from 1 to 10, said catalyst having the elements and the proportions indicated by the empirical formula:

where
A is one or more Ti, Sn, Fe, Cr, Ga
D is one or more Li, Mg, Ca, Sr, Ba, Co, Ni, Zn, Ge, Nb, Zr, Mo, W, Cu, Te, Ta, Se, Bi, Ce, In, As, B, Mn and
m is 0.8–4
a is 0.01–2
d is 0–2
x is determined by the oxidation state of the cations present,
which catalyst has been heated at a calcination temperature of at least 780° C.

2. A process of claim 1 wherein said calcination temperature is in the range from 790° C. to 1050° C.

3. A process according to claim 1 wherein A includes one or more of Sn, Ti and Fe.

4. A process of claim 3 wherein said calcination temperature is in the range from 790° C. to 1050° C.

5. A process according to claim 4 wherein A includes Sn.

6. A process of claim 1 wherein m is at least 1.2.

7. A process of claim 1 wherein m is at most 2.

8. A process of claim 1 wherein subscript a is at least 0.05.

9. A process of claim 1 wherein subscript a is at most 0.5.

10. A process of claim 1 wherein said paraffin is propane.

11. A process according to claim 7 wherein A includes one or more of Sn, Ti and Fe.

12. A process according to claim 9 wherein A includes one or more of Sn, Ti and Fe.

* * * * *